United States Patent [19]  [11]  4,069,243
DeMarinis  [45]  Jan. 17, 1978

[54] PREPARATION OF TRIFLUOROMETHYLTHIOACETIC ACID AND ITS ESTERS

[75] Inventor: Robert Michael DeMarinis, King of Prussia, Pa.

[73] Assignee: SmithKline Corporation, Philadelphia, Pa.

[21] Appl. No.: 689,426

[22] Filed: May 24, 1976

[51] Int. Cl.$^2$ .................. C07C 148/00; C07C 149/20
[52] U.S. Cl. ............................. 560/153; 260/539 R; 560/147
[58] Field of Search ..................... 260/481 R, 539 R

[56] References Cited
U.S. PATENT DOCUMENTS 3,816,533   6/1974   Brandstrom et al. ............... 260/483

OTHER PUBLICATIONS

Dehmlow, Agnew. Chem., Intn'l Ed., 13, 170-179 (1974).
Sato et al, Tetrahedron, 32, 507-513 (1976).
Moore et al, Tetrahedron, 18, 205 (1962).
Hofle et al, J.A.C.S., 93, 6307 (1971).

*Primary Examiner*—Vivian Garner
*Attorney, Agent, or Firm*—William H. Edgerton; Richard D. Foggio

[57]  ABSTRACT

A new method of preparing trifluoromethylthioacetic acid using a tertiary phosphine in a sulfur extrusion of lower alkyl trifluoromethyldithioacetate with optional is situ alkaline hydrolysis of said acetate using a biphasic hydrolysis system in the presence of a phase transfer catalyst.

9 Claims, No Drawings

PREPARATION OF TRIFLUOROMETHYLTHIOACETIC ACID AND ITS ESTERS

This invention comprises a new preparation of the important intermediate, trifluoromethylthioacetic acid, and its lower alkyl esters. The new process uses neither trifluoromethylsulfenyl chloride nor heavy metal salts such as the silver salts often used in the prior art synthetic methods.

Desulfurization of polythio or polysulfanyl organic compounds by various "extrusion" agents, including phosphorous compounds is known to the art. Triphenylphosphine is known to react with certain dithio compounds to give the corresponding thio compound but only with the acyl or vinylogous acyl disulfides. Various aminophosphines also effect this reaction over a broad field. For a review of the art, see T. Sato et al., Tetrahedron, 32; 507–513 (1976).

I have now found that certain phosphines, having three phosphorus-carbon linkages which are capable of being converted to an oxidation state of five with formation of the sulfide, react with ester derivatives of trifluoromethyldithioacetic acid to give good yields of the corresponding ester derivatives of trifluoromethylthioacetic acid. The ester portion of the products and starting materials may for convenience be limited to lower alkyl esters 1–6 carbon atoms, especially the methyl or ethyl esters. No particular advantage is evident in using more complex esters, such as aralkyl, aryl, as well as substituted or higher ester derivatives. This portion of the starting materials does not enter into the reaction therefore it may be varied widely.

Amine containing tertiary phosphines such as tri-(diethylamino)-phosphine are known to be potent sulfur-extrusion agents. Applied to the present trifluoromethyldithioacetic acid esters, these reagents give low yields of the desired thio products accompanied by much decomposition to give tarry by-products. Also the phosphorous esters, such as lower alkyl phosphites, do not react. Unexpectedly the phosphines disclosed herein react easily, in good yield and with few by-products. The reaction does not proceed readily with trichloromethyldithioacetic acid esters.

Once again, no particular advantage is evident from using more complex organic tertiary phosphines since the organic portion of the phosphine does not directly enter the reaction. For example, triphenylphosphine is very useful and is commercially available.

The phosphine reactant is therefore a tri-lower-alkyl, triphenyl or tribenzylphosphine or mixed phosphine which has a boiling point within the conditions under which the reaction is carried out and worked up. The reaction proceeds as follows:

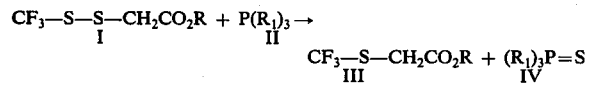

in which R is lower alkyl of from 1–6 carbon atoms, especially methyl or ethyl; and each $R_1$ is lower alkyl, phenyl or benzyl. Lower alkyl at the phosphorus atom, for convenience, may contain up to and including 10 carbon atoms.

The phosphine reagent (II) may be varied widely within the class described, for example, the preferred triphenylphosphine or substituted therefor triethylphosphine, tributylphosphine, triamylphosphine, tribenzylphosphine, tritolylphosphine, triphenethylphosphine, trianisolylphosphine, dimethylbutylphosphine, dimethylphenylphosphine, dibutylphenylphosphine, diphenylmethylphosphine, methylbenzylphenylphosphine or dibenzylphenylphosphine. Any reactive aprotic tertiary phosphines which have suitable physical characteristics such as a suitable boiling point, good stability, etc., listed in Organic Phosphorous Compounds, Volume 1, Kosolapoff et al., Wiley, Interscience 1972, pages 124 on, and which are soluble in the chosen solvent, may be used, however, the cheapest, most readily available, commercial tertiary phosphines are most useful. Others may be selected from those listed in Organic Phosphorous Compounds, etc., using the criteria described herein.

The reaction is conveniently run either with substantially equivalent molar quantities of the reactants or with an excess of the phosphine reagent in an aprotic organic solvent which is inert under the conditions of the reaction and in which the reactants are substantially soluble. The reaction may be monitored for consumption of the dithio ester compound to assess the completion of reaction or for adding more phosphine reagent. The phosphine sulfide byproduct is often formed as a crystalline product.

Most often standard organic solvents are used such as benzene, toluene, xylene, acetonitrile, ethyl ether, dioxane, tetrahydrofuran, ethyl acetate, acetone, etc. The temperature of the reaction may vary widely such as from about ice bath temperature (0°–5° C.) to the reflux temperature of the reaction mixture. Most useful is a temperature selected from the range of about 15–50° C. Conveniently the reaction is run at ambient temperature. An exothermic reaction often occurs. The time of reaction is flexible as noted above but conveniently is from the end of the exothermic reaction up to 6 hours.

The product is isolated by standard chemical methods as will be evident from the detailed examples presented hereafter. Certain of the lower alkyl esters of the product such as the methyl or ethyl esters of trifluoromethylthioacetic acid are volatile under standard stripping operations used in synthetic chemistry, especially in vacuo. For this reason special precautions or preferably immediate in situ hydrolysis of the ester may be employed.

Another aspect of this invention therefore comprises the hydrolysis of the ester product of the phosphine sulfur extrusion reaction directly in the organic reaction mixture using an aqueous solution of a standard alkali, such as an alkali metal hydroxide, for example, potassium or sodium hydroxide. Most useful is an excess of about 5–10% sodium or potassium hydroxide. The hydrolysis in the biphasic reaction is catalyzed by a phase transfer catalyst, for example, a quaternary ammonium halide, preferably the chloride or bromide, such as methyltricaprylylammonium chloride or benzyl triethylammonium chloride or a quaternary phosphonium halide such as hexadecyltributyl phosphonium bromide or chloride. Other phase transfer catalysts and conditions are listed in A. W. Herriott et al., J. Am. Chem. Soc., 97; 2345-2349 (1975); E. V. Dehmlow, Angew. Chem., Internat. Edit., 13; 170-179 (1974); C. M. Starks, J. Am. Chem. Soc., 93; 195-199 (1971); or J. Dock, Synthesis, 441-456 (1973). In fact any phase transfer catalyst capable of carrying the alkali from the aqueous layer into the organic layer may be used.

The hydrolysis is carried out by vigorously agitating the biphasic reaction mixture at temperatures from ambient temperature up to a steam bath temperature most often about 30°–70° C. The progress of the hydrolysis is monitored by vapor phase chromatography based on the ester starting material. Reaction times of from 1–12 hours are often used, although as long as 24 hours may be necessary.

The last aspect of this invention is the preparation of the starting material for the sulphur extrusion reaction, i.e., an ester of trifluoromethyldithioacetic acid. Standard reactions for exchanging chlor with fluoro atoms, such as those using antimony trifluoride-antimony pentachloride, with trichloromethyldithioacetic acid ester with or without an organic solvent with reaction times as long as several days resulted in no exchanged product.

Unexpectedly the desired fluoro for chloro exchange takes place in 15–45% yield by one of several unusual reactions. The reaction of a lower alkyl trichloromethyldithioacetate with sodium or potassium fluoride is carried out in a solid-organic solvent or aqueous-organic solvent biphasic reaction system using a phase transfer catalyst as described hereafter. In this case the catalyst must be able to carry the inorganic fluoride from either the solid or aqueous phase into the organic phase. Alternatively, the same exchange may be carried out by conventional reaction but using sulfolane as solvent.

The preferred method for producing the F for Cl exchange is the reaction of an excess of the fluoride with the desired trichloromethyl containing starting material in an organic solvent such as acetonitrile, acetone, ethyl acetate, ether, benzene, hexane, toluene at temperatures from −50° C. to room temperature, most often at ice bath to room temperature. The time of reaction depends on the scale, solvent and temperature but is usually from about 1–6 hours. The phase transfer catalyst may be any which is able to carry the alkali metal fluoride into the reaction mixture. Most preferred for the organic-solid media are the crown ethers, especially 18-crown-6, dibenzo-18-crown-16 or dicyclohexyl-18-crown-6.

Other crown ethers and their uses are described in Aldrichimica Acta, Vol. 9, No. 1, 3–12 (1976, Aldrich Chemical Co.). The latter publication described the use of fluoro for chloro exchanges in monosubstituted compounds but not $CF_3$ for $CCl_3$ in the presence of a sensitive center such as the dithio or disulfanyl group.

The liquid-liquid biphase reaction is run with an aqueous-organic liquid biphase system with an excess of alkali metal fluoride but most often at temperatures from room to steam bath or reflux temperature, most often from about 40°–70° C. In this case the preferred phase transfer catalysts are the quaternary ammonium halides or quaternary phosphonium halides as disclosed hereabove for the hydrolysis of the trifluoromethylthioacetic acid esters.

The last reaction for the F for Cl interchange is the reaction of the trichloromethyldithio ester with an excess of an alkali metal fluoride in sulfolane, usually at from room temperature to reflux temperature, but most often at about 50°–100° C. for from 1–6 hours or longer.

Of these reactions, the solid-liquid exchange reaction with crown ether as catalyst gives the best yields, is easy to run and is reproducible. The quaternary salts are, however, more commercially usable.

The following examples are designed to teach the essentials of this invention to those skilled in the art.

EXAMPLE 1

Ethyl mercaptoacetate (36.0 g., 0.3 mol) was added in portions to 55.8 g. (0.3 mol) of trichloromethylsulfenyl chloride with stirring. After stirring for one hour the mixture was distilled to give 68.5 g. of a yellow oil boiling at 94°–96° C. at 0.25 mm. Hg. (84.5% of trichloromethyldithioacetic acid, ethyl ester).

Substituting other esters, such as methyl, propyl, butyl, 2-hexyl or benzyl for the ethyl mercaptoacetate starting material gives the corresponding ester derivatives of trichloromethyldithioacetic acid. These may then be substituted in molar equivalent quantities in the following reactions.

EXAMPLE 2

18-Crown-6 (1.58 g., 0.006 mol) was dissolved in 20 ml. of dry benzene then stirred while 4.06 g. (0.07 mol) of commercial anhydrous potassium fluoride was added. The suspension was stirred for 60 minutes. A solution of 5.40 g. (0.02 mol) of ethyl trichloromethyldithioacetate in 5 ml. of benzene was added. The mixture was heated at reflux for 2.5 hours. The reaction mixture was cooled, filtered, stripped and distilled to give a tan oil boiling at about 85° C. (aspirator pressure), (1.50 g., 34.1% of ethyltrifluoromethyldithioacetate).

EXAMPLE 3

A mixture of 6.96 g. (0.12 mol) of potassium fluoride and 1.58 g. (0.006 mol) of 18-crown-6 in 50 ml. of dry acetonitrile was stirred for 30 minutes after which 5.40 g. (0.02 mol) of methyl trichloromethyldithioacetate in 10 ml. of acetonitrile is added. The mixture is stirred at room temperature for 2 hours. The reaction residue was distilled to give 1.76 g. of oil boiling at 79°–84° C. (aspirator), (40.9% of ethyl trifluoromethyldithioacetate).

The reaction was run at −40° to −10° C., then up to room temperature for 30 minutes to give 34.1% of product, b.p. 79°–83° C.

The reaction was run in acetone at −50° to −40° C. then up to 0° C. to give 32.7% of product, b.p. 79°–80° C.

The reaction was run in acetonitrile at 0°–10° C. for 2.5 hours, then at room temperature for 2 hours to give 40.9% of product.

EXAMPLE 4

A mixture of 5.04 g. (0.12 mol) of sodium fluoride and 5.40 g. (0.02 mol) of ethyl trichloromethyldithioacetate in 50 ml. of hexane and 50 ml. of distilled water with 200 mg. of methyl tricaprylylammonium chloride ("Aliquat 336") in 10 ml. of hexane is stirred at room temperature overnight. The hexane layer was dried and concentrated to give 1.40 g. of oil (35%) after purification over silica gel.

The reaction was repeated at 60°–65° C. for one hour to give a lower yield of trifluoromethyldithioacetic acid ester.

EXAMPLE 5

A mixture of 13.4 g. (0.72 mol) of ethyl trichloromethyldithioacetate is added to a warm mixture (50° C) of 13.4 g. of sodium fluoride (0.32 mol) in 50 ml. of sulfolane with stirring. The mixture is stirred vigorously at 100° C. for 1.5 hours. The reaction mixture is gradually heated to 175° C. under an aspirator. The distillates were combined and redistilled to give 4.90 g. (31%) of the trifluoromethyldithioacetic acid ester.

EXAMPLE 6

A stirred solution of 2.88 g. (11 mmol) of triphenylphosphine in 25 ml. of dry ether was reacted by the dropwise addition of 2.20 g. (10 mmol) of ethyl trifluoromethyldithioacetate in 10 ml. of ether. The suspension was stirred for one hour at room temperature. After filtration the ether was removed. The residue was washed with petroleum ether. The petroleum ether was gathered and concentrated to give 0.72 g. (38.3%) of trifluoromethylthioacetic acid ethyl ester. Further purification may be carried out over a silica gel column with hexane.

The same reaction was carried out in benzene at reflux for ½ hour and at room temperature for two hours followed by reflux for ½ hour.

EXAMPLE 7

A solution of 4.40 g. (20 mmol) of ethyl trifluoromethyldithioacetate in 20 ml. of ether was added dropwise to a stirred solution of 5.76 g. (21 mmol) of triphenylphosphine in 50 ml. of dry ether. The reaction was stirred at room temperature for 75 minutes. Tetrahydrofuran (50 ml.) was added. The stirred mixture became homogeneous. A solution of 25 ml. of 10% sodium hydroxide solution was added followed by 400 mg. of methyl tricaprylylammonium chloride in 5 ml. of tetrahydrofuran. The mixture was stirred vigorously at 40°–50° C. for two hours. An additional 20 ml. of 10% sodium hydroxide was added with 200 mg. of the catalyst. The reaction was continued for six hours at 40°–50° C. The mixture was diluted with 350 ml. of water and the organic layer separated. The aqueous phase is made acid with 3 N hydrochloric acid then extracted with ether. The residue from the dried ether extracts was distilled at the aspirator to give 1.89 g. of yellow oil at 95°–99° C. (59.4% of trifluoromethylthioacetic acid).

The reaction was repeated with 5.76 g. of triphenyl phosphine and 4.40 g. of dithio ester in 50 ml. of benzene at ambient temperature followed by hydrolysis with 40 ml. of 5% sodium hydroxide and 400 mg. of catalyst at 50°–60° C. for 2.5 hours. Working up as above gave 1.03 g. of acid boiling at 89°–90° C., (32.2%).

The reaction was run in tetrahydrofuran to give, after hydrolysis with 5% sodium hydroxide at ambient temperature, 59.3% of the acid boiling at 89°–90° C.

EXAMPLE 8

Repeating the reaction of Example 7, using 4.40 g. of the dithioester and 4.40 g. of tri-n-butylphosphine in benzene with hydrolysis by 5% sodium hydroxide and 500 mg. of catalyst at 60° C. for three hours gave 2.76 g. of oil boiling at 90°–91° C. (23.8%).

EXAMPLE 9

Substituting the methyl, propyl, butyl, 2-hexyl or benzyl esters of trichloromethyldithioacetic acid of Example 1 in the procedures of Examples 2, 6 or 7 gives the corresponding trifluoromethyldithio-and thio-acetic acid esters as well as the acids.

Also, an excess of any of the tertiary phosphines listed here above may be substituted for triphenylphosphine in Example 7 with minor adjustments within the skill of the art.

What is claimed is:

1. The method of preparing lower alkyl esters of trifluoromethylthioacetic acid comprising reacting a lower alkyl ester of trifluoromethyldithioacetic acid with a tertiary phosphine of the structure:

$$P(R_1)_3$$

in which each $R_1$ is lower alkyl having not more than 10 carbon atoms, phenyl or benzyl in an aprotic organic solvent in which the reactants are soluble and which is inert under the reaction conditions.

2. The method of claim 1 in which the tertiary phosphine is triphenylphosphine.

3. The method of claim 2 in which the reaction is carried out at ambient temperature.

4. The method of claim 2 in which the lower alkyl ester is the ethyl ester.

5. The method of claim 3 in which the lower alkyl ester is the ethyl ester.

6. The method of preparing trifluoromethylthioacetic acid comprising reacting a lower alkyl ester of trifluoromethyldithioacetic acid with a tertiary phosphine of the structure:

$$P(R_1)_3$$

in which each $R_1$ is lower alkyl having not more than 10 carbon atoms, phenyl or benzyl in an aprotic organic solvent in which the reactants are soluble and which is inert under the reaction conditions to obtain a lower alkyl trifluoromethylthioacetic acid ester and hydrolyzing said ester by contacting the reaction product mixture containing said ester with an aqueous solution of sodium or potassium hydroxide in the presence of a phase transfer catalyst capable of carrying said hydroxide into the organic phase.

7. The method of claim 6 in which said phase transfer catalyst is a quaternary ammonium halide.

8. The method of claim 7 in which said phase transfer catalyst is methyl tricaprylylammonium chloride.

9. The method of claim 7 in which the organic solvent of the reaction mixture is benzene, ethyl ether or tetrahydrofuran and the ester is the ethyl ester.

* * * * *